(12) United States Patent
Lombardi, III et al.

(10) Patent No.: US 9,695,966 B2
(45) Date of Patent: Jul. 4, 2017

(54) QUICK CONNECT FLUID CONDUIT CONNECTOR HAVING LATCH WITH INTEGRAL SPRING ARMS FOR BUTTON RELEASE

(71) Applicant: Nordson Corporation, Westlake, OH (US)

(72) Inventors: Francis J. Lombardi, III, Erie, CO (US); Derrick S. Sjodin, Bloomfield, CO (US)

(73) Assignee: Nordson Corporation, Westlake, OH (US)

( * ) Notice: Subject to any disclaimer, the term of this patent is extended or adjusted under 35 U.S.C. 154(b) by 304 days.

(21) Appl. No.: 14/474,676

(22) Filed: Sep. 2, 2014

(65) Prior Publication Data

US 2015/0076815 A1 Mar. 19, 2015

Related U.S. Application Data

(60) Provisional application No. 61/877,673, filed on Sep. 13, 2013.

(51) Int. Cl.
*F16L 39/00* (2006.01)
*F16L 37/084* (2006.01)
*A61M 39/10* (2006.01)

(52) U.S. Cl.
CPC ......... *F16L 37/0841* (2013.01); *A61M 39/10* (2013.01); *A61M 39/1011* (2013.01);
(Continued)

(58) Field of Classification Search
USPC ........................................... 285/317, 81, 82
See application file for complete search history.

(56) References Cited

U.S. PATENT DOCUMENTS 5,316,041 A * 5/1994 Ramacier, Jr. ...... F16L 37/0841
137/614.04
5,695,223 A * 12/1997 Boticki .................. F16L 37/40
285/23
(Continued)

FOREIGN PATENT DOCUMENTS

FR 2906341 A3 3/2008
WO 0053966 A1 9/2000

OTHER PUBLICATIONS

European Patent Office, European Search Report in EP Application No. 14184396, Oct. 29, 2014.
(Continued)

*Primary Examiner* — Aaron Dunwoody
(74) *Attorney, Agent, or Firm* — Baker & Hostetler LLP

(57) ABSTRACT

A quick connect fluid conduit connector includes male and female connector components that releasably engage with each other to fluidically connect two fluid conduits. The female connector component defines a receptacle for receiving a distal end of the male connector component, and a latch in the female connector component is configured to engage with a latch catch groove on the male connector component to reliably secure these components together in a sealed coupling. The latch is a unitary piece having a large release button integrally formed with multiple spring arms, thereby simplifying assembly of the fluid conduit connector and providing redundancy against failure modes. In addition, the female connector component may also include a lock mechanism engaged with the latch for providing additional protection against unintentional disconnection of the male and female connector components.

24 Claims, 9 Drawing Sheets

(52) U.S. Cl.
CPC .. *A61M 2039/1027* (2013.01); *F16L 2201/20* (2013.01); *F16L 2201/60* (2013.01)

(56) References Cited

U.S. PATENT DOCUMENTS

| | | | |
|---|---|---|---|
| 5,845,943 | A | 12/1998 | Ramacier, Jr. et al. |
| 6,626,465 | B2 * | 9/2003 | Lacroix ............... F16L 37/0841 285/308 |
| 7,159,797 | B1 * | 1/2007 | Lammers ............. B05B 15/065 239/390 |
| 8,231,145 | B2 * | 7/2012 | Blivet ................. F16L 37/0841 285/288.1 |
| 8,764,068 | B2 * | 7/2014 | Frick .................. F16L 37/0841 285/308 |
| 2011/0204621 | A1 | 8/2011 | Whitaker et al. |
| 2011/0204622 | A1 | 8/2011 | Lewis et al. |
| 2011/0210541 | A1 * | 9/2011 | Lewis ................. F16L 37/0841 285/317 |
| 2013/0092271 | A1 | 4/2013 | Downs et al. |

OTHER PUBLICATIONS

Colder Products Company, The MPC Quick Connect, Brochure, 2011, 1 pg.
Colder Products Company, MPC/MPX Back-to-Back Adapters, Brochure, 2013, 1 pg.

* cited by examiner

QUICK CONNECT FLUID CONDUIT CONNECTOR HAVING LATCH WITH INTEGRAL SPRING ARMS FOR BUTTON RELEASE

CROSS-REFERENCE TO RELATED APPLICATION

This application claims the priority of U.S. Provisional Patent Application Ser. No. 61/877,673, filed on Sep. 13, 2013, the disclosure of which is incorporated by reference herein.

TECHNICAL FIELD

The present invention generally relates to fluid conduit connectors, and more particularly, to male and female components of a fluid conduit connector having latching and/or locking features to retain the male and female components together.

BACKGROUND

A variety of quick connect/disconnect coupling assemblies for small flexible tubing applications and other fluid conduit applications are known for use when multiple sections of fluid conduit or tubing need to be connected together. For example, such coupling assemblies are utilized for bio-medical applications, convenience handling, beverage dispensing, instrument connections, photochemical handling, etc. The coupling assemblies typically include male and female connector components that releasably couple to each other to retain the multiple sections of fluid conduit or tubing in fluid communication. Typically, these male and female connector components are subject to axial and side loads applied to one or both of the multiple sections of fluid conduit or tubing. In addition, the male and female connector components must remain secured together in a sealed relationship regardless of the loading applied, and preferably until a user intentionally actuates the disconnection of the male and female connector components from one another.

One particular known design for the male and female connector components includes a latch on one of these components that engages with a latch catch on the other of these components to secure the fluid conduit connector together. The latch is biased to a latched position by spring elements in some embodiments. As a result, both the latch and the spring elements must be assembled to one of the male and female connector components, and this can be a time-consuming and expensive manufacturing process. Moreover, if the latch and spring elements are not precisely aligned and connected to the connector component, the fluid conduit connector will likely fail when presented with loading in one or both of the axial and side load directions. In an effort to add security to the latched connection between the male and female connector components, some fluid conduit connectors are manufactured such that even the intentional unlatching and disconnection of the connector components is exceedingly difficult to perform.

For reasons such as these, there is a need for a quick connect fluid conduit connector that offers improved coupling security, simplified operation, and decreased manufacturing costs.

SUMMARY

In one embodiment, a quick connect fluid conduit connector includes a male connector component and a female connector component configured to be coupled to one another. The male connector component includes a male distal end configured to receive a seal member, a first fluid conduit defined by a first elongate bore extending from the male distal end, and a latch catch groove adjacent to a radially projecting latching flange which is located proximal from the male distal end. The female connector component includes a connector housing defining a female distal end and a receptacle extending proximally from an opening in the female distal end, a second fluid conduit defined by a second elongate bore, and a latch operatively engaged with the connector housing and configured to retain the male connector component. The latch includes a release button positioned along a top side of the connector housing, a latch plate extending from the release button at least partially across said receptacle so as to latch into engagement with the male connector component, and at least one spring arm integrally formed as a unitary piece with the release button and extending into the connector housing. Engaged with the connector housing, the spring arm biases the latch towards a latched position in which the latch plate engages the latch catch groove to prevent removal of the male connector component from the receptacle. The release button is configured to be depressed into the connector housing to move the latch against the bias and towards an unlatched position in which the latch plate disengages from the latch catch groove. Furthermore, the female connector component also includes a lock mechanism having a lock slider operatively engaged with the latch. The lock slider is movable between a locked position, in which movement of the latch towards the unlatched position is prevented, and an unlocked position where operation of the latch is unaffected.

According to one aspect, the latch includes multiple spring arms integrally formed with the release button, such that a redundant bias force is applied to the latch towards the latched position. As a result, the fluid conduit connector enables easy one-step assembly of the latch with the female connector component and protection against failure modes. The receptacle also includes a tapered lead-in bore section that extends proximally from the latch plate. The tapered lead-in bore section reduces any frictional engagement between the receptacle and the seal member on the male distal end during insertion or removal of the male connector component. Therefore, the male and female connector components are easier to move when a user intends to connect or disconnect the corresponding fluid conduits.

The male and female connector components also include features that assist with transfer or bearing of loads applied to the connector components. To this end, the opening in the female distal end is bounded by a generally annular periphery and the male connector component includes a plurality of lugs that are positioned to engage this generally annular periphery when the male and female connector components are secured together. The plurality of lugs are positioned proximal to the latch catch groove, which is how the lugs are accurately located relative to the opening in the female distal end, which is also positioned adjacent to the latch plate that enters the latch catch groove. The lugs are configured to transfer radial or side loads from one connector component to the other. Adjacent to the lugs on the male connector component is a radially extending grip flange. This grip flange is positioned adjacent to or in abutting relation with the female distal end when the male and female connector components are secured together. As a result, the grip flange and female distal end transfer axial loads between the connector components. This at least partial bearing of loads protects the latch from having to bear all loads applied to the fluid conduit connector.

The latch plate includes an occluding portion that extends at least partially across the receptacle in the latched position, and this latch plate is also engaged with a latch track formed by standoffs in the connector housing to prevent the latch from moving upwardly beyond the latched position. More specifically, the latch track includes detents that opposing projections of the latch plate snap into engagement with during assembly of the latch with the remainder of the female connector component. This latch track also ensures that the latch plate and the release button move upwardly and downwardly in a transverse direction to an axial movement direction of the male connector component.

The connector housing is provided with a clean and smooth contoured appearance that provides beneficial operation for a user of the fluid conduit connector. To this end, the connector housing includes a contoured button shroud defining a top side of the connector housing that surrounds any sharp edges and corners presented by the release button. By eliminating any exposed pinch points or sharp contours, the male and female connector components are less likely to be caught on a user's clothing or other equipment. The connector housing also defines a finger groove opposite the release button to provide relatively large gripping surfaces for the user to operate the female connector component and latch with a single hand. Thus, a sensation or impression of needing less force to actuate the release button is provided to the user.

In some aspects, at least one lock lug extends downwardly from the lock slider through lug apertures provided in a modified release button. The lock lugs include a retention detent that snaps into engagement with a fin or some other shoulder provided adjacent to the lug apertures to thereby hold the lock mechanism on the latch. The lock lugs are positioned directly over a standoff inside the connector housing in the locked position, and the engagement of the lock lugs with this standoff prevents operation of the latch in the locked position. The lock lugs are spaced from that standoff in the unlocked position so that the lock lugs and the release button of the latch are free to move downwardly towards the unlatched position.

The lock mechanism may include visual indicia on one or both of the release button and the lock slider, to thereby provide information to a user on what state the lock mechanism is in. The lock mechanism also includes a spring pin that extends downwardly from the lock slider into engagement with a shaped aperture provided in the modified release button. The shaped aperture or the spring pin must be deformed to move the lock slider between the two positions (locked and unlocked). As a result, the lock mechanism avoids accidental engagement or disengagement, thereby enhancing the operability of the lock mechanism and also of the fluid conduit connector.

These and other objects and advantages of the invention will become more readily apparent during the following detailed description taken in conjunction with the drawings herein.

BRIEF DESCRIPTION OF THE DRAWINGS

The accompanying drawings, which are incorporated in and constitute a part of this specification, illustrate embodiments of the invention and, together with a general description of the invention given above, and the detailed description of the embodiments given below, serve to explain the principles of the invention.

DETAILED DESCRIPTION

Figure 1:
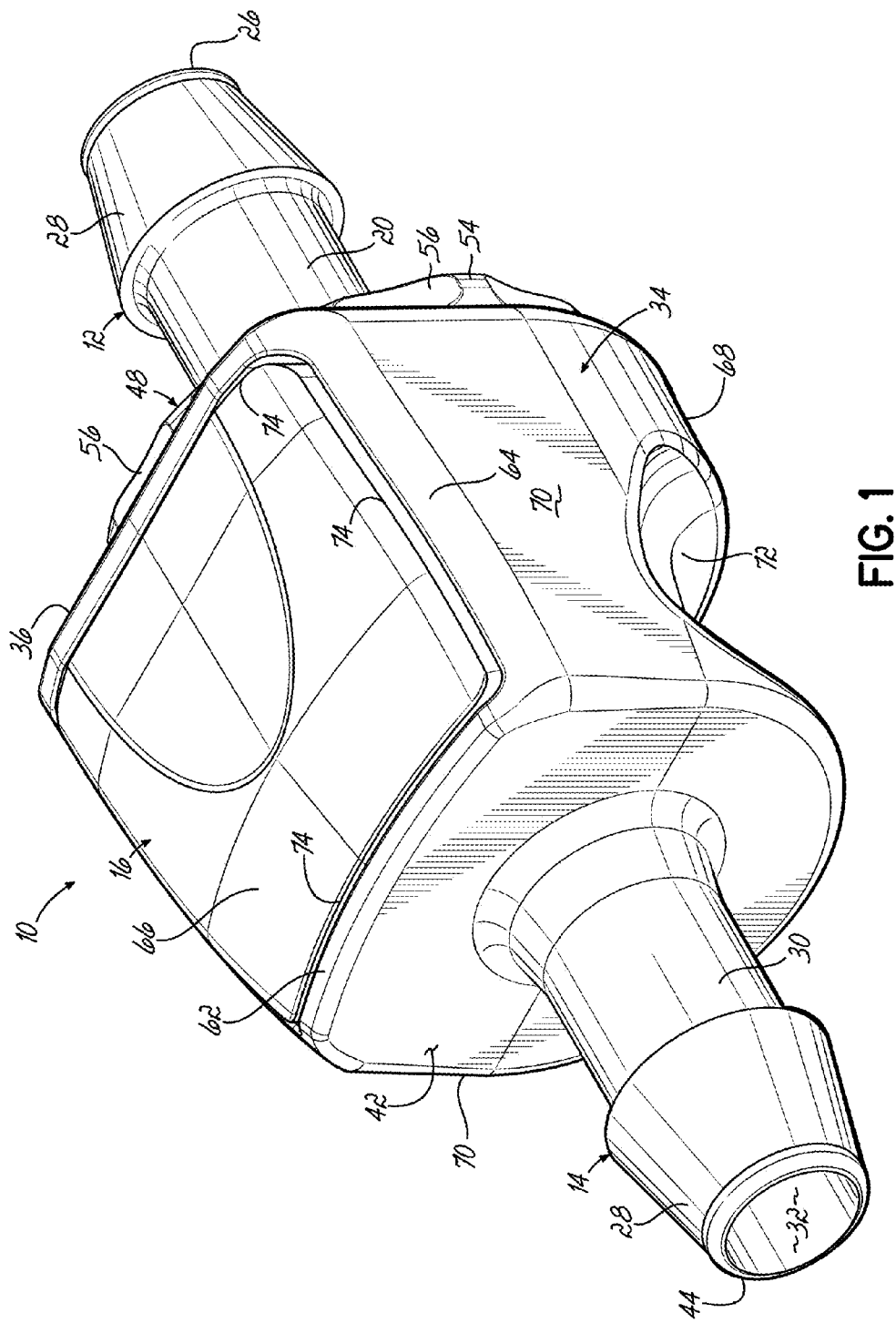
FIG. 1 is a perspective view of a quick connect fluid conduit connector according to a first embodiment of the present invention, with male and female connector components engaged with one another.

Referring to FIGS. 1 through 7B, a quick connect fluid conduit connector 10 in accordance with one embodiment of the present invention is optimized to retain a male connector component 12 and a female connector component 14 together regardless of any axial or side loading applied to tubing or flexible conduits that may be coupled to the male and female connector components 12, 14. To this end, the female connector component 14 includes a latch 16 that reliably retains the male connector component 12 in various operating conditions while making simple the process for disconnecting the male and female connector components 12, 14 from each other. Furthermore, the male and female connector components 12, 14 are designed for quick and simple manufacturing, and these elements include redundant structures to minimize the likelihood of failure during operation. Accordingly, the fluid conduit connector 10 provides several advantages compared to known connector assemblies.

Figure 2:
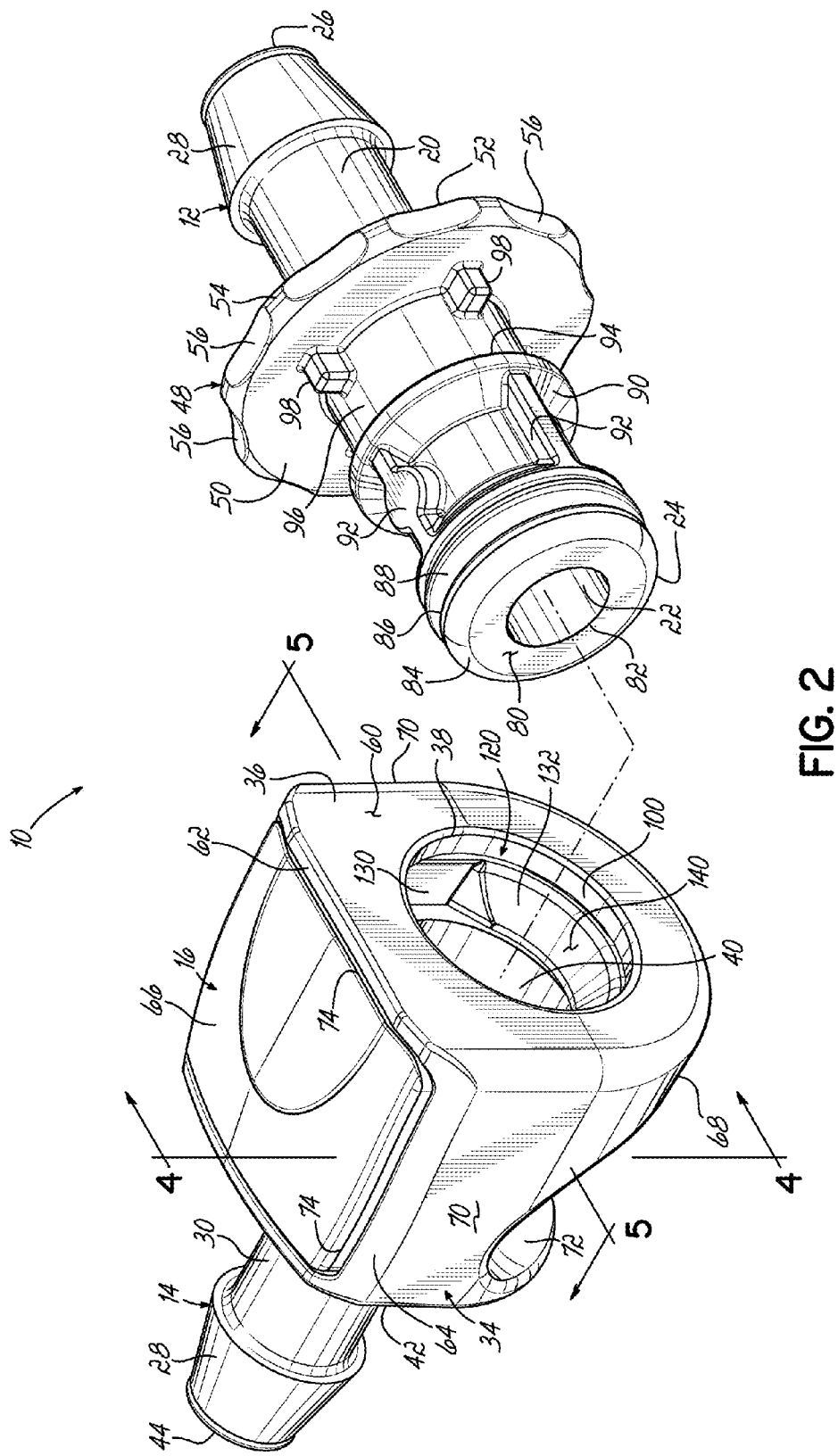
FIG. 2 is a perspective view of the fluid conduit connector of FIG. 1, where the male and female connector components have been disconnected from one another.

With particular reference to FIGS. 1 and 2, the male and female connector components 12, 14 of this embodiment of the fluid conduit connector 10 are shown in a connected state as well as a disconnected state. The male connector component 12 includes a first fluid conduit 20 defined by a first elongate bore 22 extending along an axial or longitudinal length of the male connector component 12. To this end, the first elongate bore 22 extends from a male distal end 24 to a male proximal end 26 of the male connector component 12. The male proximal end 26 of the male connector component 12 includes a conventional hose barb 28 or some other similar structure for connecting to and retaining a portion of flexible tubing or similar fluid conduits (not shown). Thus, the male connector component 12 becomes an end piece of the portion of flexible tubing when that flexible tubing is connected to the hose barb 28 at the male proximal end 26.

It will be appreciated that the use of the terms "distal and proximal" throughout this specification and the claims is intended to provide a frame of reference for each element of these male and female connector components 12, 14. More specifically, "distal" refers to a direction towards the other connector component 12, 14 when the male and female connector components 12, 14 are secured to each other, and this direction is also away from the portion of flexible tubing or conduit that is coupled to the male or female connector component 12, 14. Likewise, "proximal" refers to a direction away from the other connector component 12, 14 and towards the connected portion of flexible tubing or conduit. Furthermore, "axial" is used to refer to lengths and movements along or parallel to a longitudinal axis through the male and female connector component 12, 14, while "radial" is used to refer to a direction perpendicular to the axial direction.

Returning to FIGS. 1 and 2, the female connector component 14 includes a second fluid conduit 30 defined by a second elongate bore 32. The female connector component 14 also includes a connector housing 34, which is where the latch 16 briefly described above is located. The connector housing 34 is a generally hollow body defining a female distal end 36 with an opening 38 that provides access into a receptacle 40 extending axially into the connector housing 34. The receptacle 40 is elongate and is configured to receive the male distal end 24 of the male connector component 12. In this regard, the receptacle 40 extends from the opening 38 proximally into fluid communication with the second elongate bore 32. Similarly, the second fluid conduit 30 extends between a proximal face 42 of the connector housing 34 and a female proximal end 44 of the female connector component 14, which includes a conventional hose barb 28 or similar structure just like the male proximal end 26. After the male and female connector components 12, 14 are secured to one another, the flexible tubing or conduit (not shown) connected to each of the hose barbs 28 is brought into fluid communication via the first and second elongate bores 22, 32, which collectively extend between the hose barbs 28 in the assembled state shown in FIG. 1. As such, the fluid conduit connector 10 provides a simple-to-use two-component sealed connection between two portions of flexible tubing or conduits.

Each of the male and female connector components 12, 14 include structural features configured to enhance the ability of a user to hold and actuate the connection and disconnection of the fluid conduit connector 10. More particularly, the male connector component 12 includes a radially extending grip flange 48 located about halfway along the length between the male distal end 24 and the male proximal end 26. The grip flange 48 in the illustrated embodiment is shaped substantially as a cylindrical or annular plate having relatively large distal and proximal faces 50, 52 and a contoured edge 54 extending between the distal face 50 and proximal face 52. The contoured edge 54 includes a series of about ten concave or flat finger grips 56 around a generally annular periphery. It will be understood that while the grip flange 48 is shown with the cylindrical shape and ten finger grips 56 in this embodiment, the shape and the number of finger grips may be modified in other embodiments without departing from the scope of the invention. A user may readily grasp the male connector component 12 at the grip flange 48 in order to move the male connector component 12 towards and away from engagement with the female connector component 14.

The female connector component 14 is also optimized for manual grasping, specifically at the connector housing 34. The connector housing 34 has a generally U-shaped cross section extending along an axial length between a distal face 60 located at the female distal end 36 and the proximal face 42 at the opposite end of the connector housing 34. Thus, the connector housing 34 includes a generally flat top side 62 defined by a button shroud 64 surrounding a generally planar release button 66 of the latch 16, a rounded bottom surface 68, and generally planar sidewalls 70 extending between the button shroud 64 and the rounded bottom surface 68. The rounded bottom surface 68 further includes a finger groove 72 projecting inwardly towards the top side 62 of the connector housing 34. The finger groove 72 is shaped and sized to receive one or more fingers of a user when the user manually grasps the female connector component 14, thereby enhancing the grip available when moving the female connector component 14. To this end, the shape of the finger groove 72 is tailored to encourage proper finger placement for a user grasping the female connector component 14. Additionally, the finger groove 72 is conveniently located opposite the release button 66 of the latch 16 so that a user can be provided with a suitable grip for generating leverage when actuating the latch 16 by depressing the release button 66.

Each of the release button 66 and the finger groove 72 advantageously extends over a relatively large portion or majority of the axial length of the connector housing 34 as defined between the proximal face 42 and the distal face 60. The relatively large size of the release button 66 and the finger groove 72 provide broad surface areas for actuating the latch 16 as described in further detail below, leading to a smoother button operation with perceived less force needing to be applied (the latch opening force is applied over a larger surface area, thereby giving a sensation or impression to the user of a lower force over a larger area). With one hand on the grip flange 48 of the male connector component 12 and another hand on the finger groove 72 and release button 66, a typical user will be enabled to easily control operation and movement to connect and disconnect the fluid conduit connector 10.

The connector housing 34 of the female connector component 14 is also contoured to enhance a user's ability to manually grasp and reliably operate the fluid conduit connector 10. More specifically, the various edges between the proximal face 42, sidewalls 70, bottom surface 68, and distal face 60 are all rounded to avoid presenting any sharp corners or edges that clothing or other equipment may become caught on. Similarly, the interfaces of the connector housing 34 with the finger groove 72, the second fluid conduit 30, and the release button 66 are also rounded and present no sharp corners or edges. For example, the release button 66 includes generally sharp corners and edges 74 around a periphery of the planar release button 66 in the illustrated embodiment, but these sharp corners and edges 74 are surrounded and substantially covered by the contoured button shroud 64. Thus, the connector housing 34 is provided with a smooth, clean appearance while also functionally protecting from exposing sharp edges 74 or pinch points that would otherwise be potential problem zones when using the fluid conduit connector 10 and during movement of the latch 16 between latched and unlatched positions. It will be understood that the particular contoured profile of the connector housing 34 may be altered in other embodiments consistent with the present invention.

Figure 3:
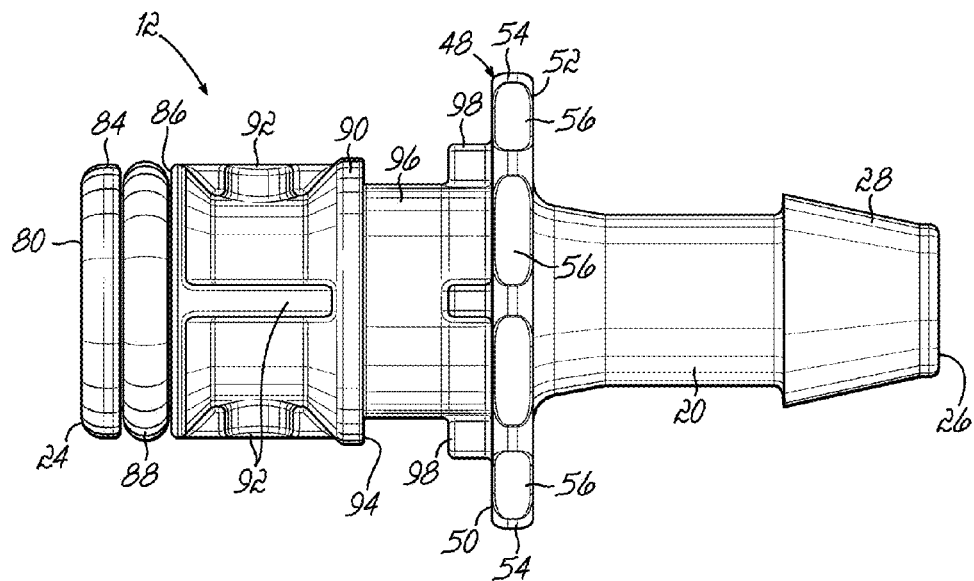
FIG. 3 is a side elevation view of the male connector component of FIG. 2.

With specific reference to FIGS. 2 and 3, the external profile and features of the male connector component 12 used with this embodiment of the fluid conduit connector 10 are shown. These external features are the relevant distinguishing features provided on the male connector component 12, as the first elongate bore 22 is substantially continuous and uninterrupted along the entire axial length of the male connector component 12. Furthermore, these features described below are tailored to be handled by the user or interact with the latch 16 and the female connector component 14 to thereby produce the sealed coupling of tubing or conduits connected to the hose barbs 28 of the male and female connector components 12, 14.

Starting at the male distal end 24, the male connector component 12 includes a distal surface 80 defining an opening 82 into the first elongate bore 22 and a seal flange 84 defined by an outer periphery of the male distal end 24 extending proximal from the distal surface 80. The seal flange 84 includes an annular seal groove 86 configured to receive a seal member 88 therein. In the embodiments of the fluid conduit connector 10 shown, the seal member 88 is an elastomeric O-ring seal, although it will be understood that other types and materials of seals may be used for the seal member 88. This seal member 88 is configured to engage into sealed contact with the receptacle 40 in the female connector component 14 when the male and female connector components 12, 14 are secured to each other. As described in further detail below, the seal member 88 therefore prevents leakage of fluids or pressure moving through the first and second elongate bores 22, 32 when the fluid conduit connector 10 is fully assembled.

Continuing in a proximal direction from the seal member 88 and seal groove 86, the seal flange 84 is connected to a latching flange 90 by a series of ribs 92 or other structure forming a generally continuous radial dimension or profile for the first fluid conduit 20 between the distal surface 80 and the latching flange 90. The latching flange 90 defines a shoulder 94 delimiting one side of a latch catch groove 96 formed on the male connector component 12. The latch catch groove 96 is delimited on an opposite side by a plurality of lugs 98 proximal to the latch catch groove 96 and projecting radially outwardly from the first fluid conduit 20. The latch catch groove 96 is positioned to receive a portion of the latch 16 to prevent further relative movements of the male and female connector components 12, 14 after the assembly of the fluid conduit connector 10. As discussed above, the seal flange 84, ribs 92, and latching flange 90 form a generally continuous radial profile so that the relevant portion of the latch 16 may ride over these elements without becoming stuck before the latch 16 engages with the latch catch groove 96. It will be understood that the specific shapes of the seal flange 84, latching flange 90, and ribs 92 may be modified in other embodiments and also that the ribs 92 may be replaced by alternative structure extending between the flanges 84, 90 without departing from the scope of the invention.

The plurality of lugs 98 delimiting the other side of the latch catch groove 96 are also positioned adjacent to the distal face 50 of the grip flange 48. As a result, the lugs 98 and the grip flange 48 are positioned at the opening 38 into the receptacle 40 and at the distal face 60 of the connector housing 34, respectively, when the fluid conduit connector 10 is assembled by latching the male and female connector components 12, 14 together. This arrangement of the lugs 98 and the grip flange 48 provides potential structural connections of the male and female connector components 12, 14 that may be used to transfer some axial and side loading on these connector components 12, 14 without relying on just the latch 16 and latch catch groove 96 to transfer those loads. More particularly, the lugs 98 engage or contact a slightly conical annular periphery 100 presented by the opening 38 at the female distal end 36 to at least partially transfer loads when one or both of the male and female connector components 12, 14 is subject to side loading. Similarly, the distal face 50 of the grip flange 48 is positioned to engage or contact the distal face 60 of the connector housing 34 to at least partially transfer loads when one or both of the male and female connector components 12, 14 is subject to axial loading. It will be understood that while four lugs 98 are shown in this exemplary embodiment of the male connector component 12, more or fewer lugs 98 may be provided in other embodiments.

Figure 4:
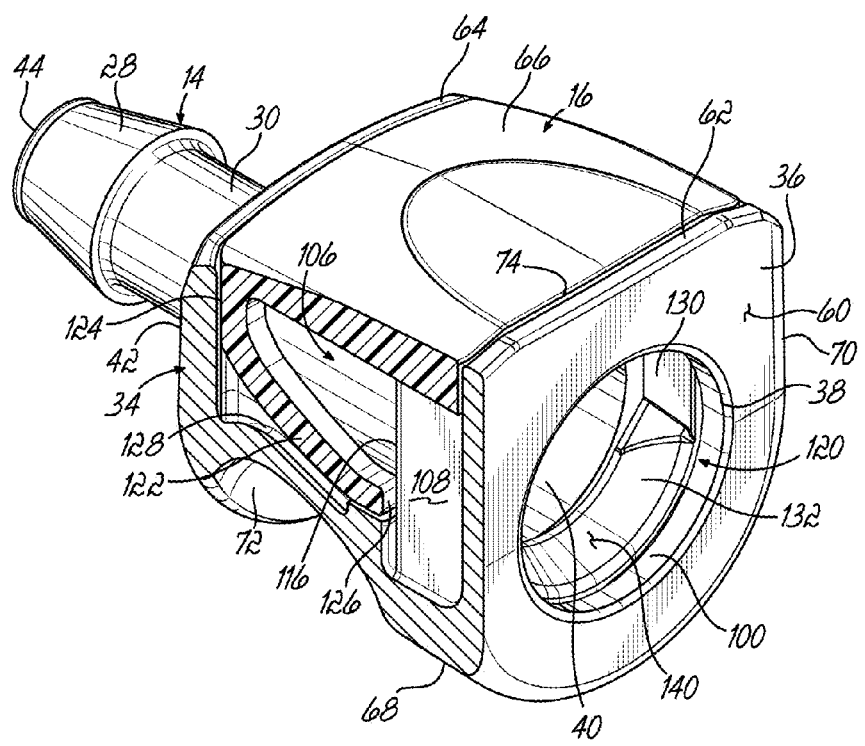
FIG. 4 is a perspective view of the female connector component of FIG. 2, with the view partially sectioned along line 4-4 in FIG. 2 to reveal internal components of a connector housing and a latch of the female connector component.
Figure 5:
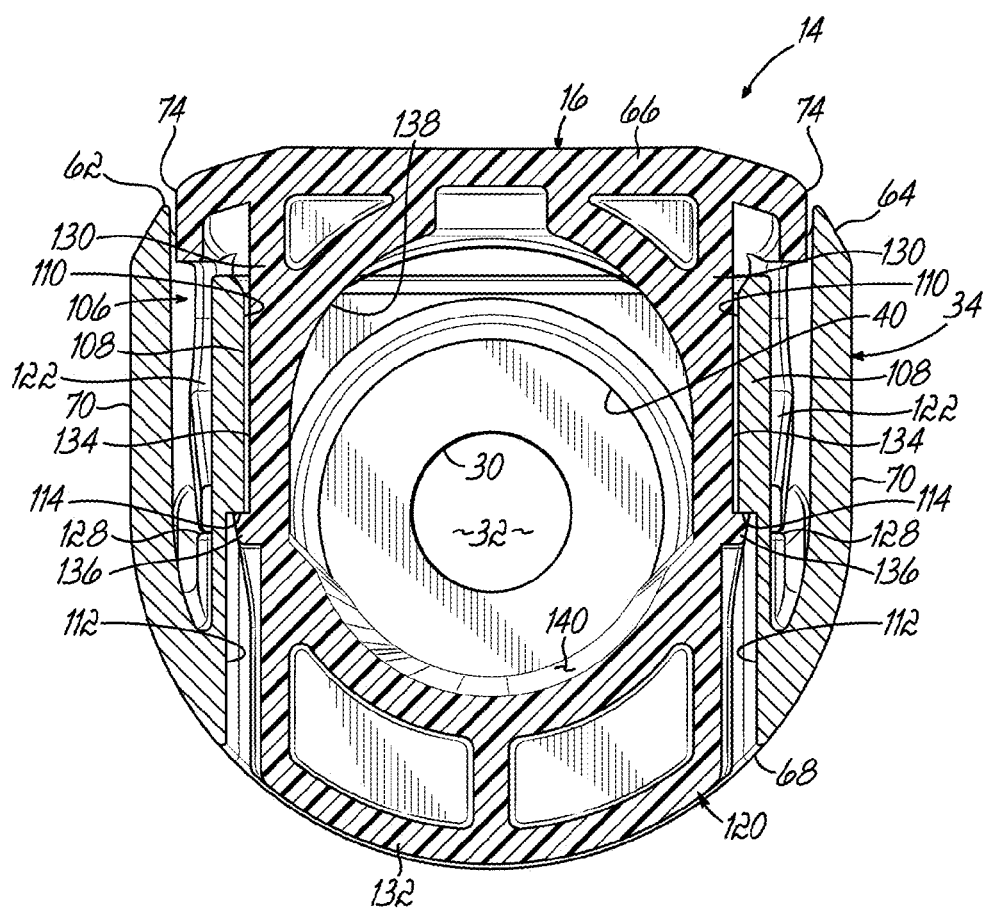
FIG. 5 is a cross-sectional end view of the female connector component along line 5-5 in FIG. 2, thereby revealing additional aspects of the latch and connector housing also shown in FIG. 4.

Now with reference to FIGS. 4 and 5, additional features of the latch 16 and the connector housing 34 of the female connector component 14 are shown. As discussed briefly above, the connector housing 34 is a substantially hollow body defined by a hollow receptacle 40 extending axially and located within an interior cavity 106 which is bounded by the proximal face 42, the distal face 60, the sidewalls 70, and the rounded bottom surface 68 of the connector housing 34. The interior cavity 106 is larger than the receptacle 40, which forms a clearance configured to receive portions of the latch 16 described below. Within this interior cavity 106, a pair of standoffs 108 is located just proximally from the female distal end 36. The standoffs 108 could be replaced by a single standoff in other embodiments. The pair of standoffs 108 radially inward facing surfaces 110 defining a latch track 112 configured to receive a portion of the latch 16. The latch track 112 includes opposing detents 114 or shoulders used to retain the latch 16 as described in further detail below. The latch track 112 is positioned in an axial gap located between the female distal end 36 (and its opening 38) and the receptacle 40, this axial gap sized to receive a portion of the latch 16.

The standoffs 108 also extend outwardly from the receptacle 40 and inwardly from the sidewalls 70 of the connector housing 34, and thereby also include an abutment surface 116 facing proximally towards the interior cavity 106 surrounding the receptacle 40. The abutment surface 116 is also configured to interact with yet another portion of the latch 16, as described below. The precise positioning of the standoffs 108 with the inwardly facing surfaces 110 and the abutment surface 116 is shown in further detail in the cross sections shown in FIGS. 4 and 5.

The latch 16 includes the release button 66 located along and substantially surrounded by the flat top side 62 of the connector housing 34. The latch 16 also includes a latch plate 120 that extends downwardly from the release button 66 adjacent to the female distal end 36 so as to extend through the axial gap defined by the latch track 112. Also extending downwardly from the release button 66 on either lateral side of the receptacle 40 are two spring arms 122 integrally formed with the remainder of the latch 16. To this end, the components of the latch 16 (e.g., the release button 66, the latch plate 120 and the spring arms 122) are unitarily formed as a single piece out of a material with some inherent resiliency, such as plastics or composites. In some embodiments, the latch 16 may be molded as an integral piece from polycarbonate and/or polypropylene materials. Similar materials are also used for the male and female connector components 12, 14 as well in this embodiment. The inherent resiliency of the material used to form the latch 16 results in the spring arms 122 providing a restoring or biasing force when deflected from an original position. To this end, the spring arms 122 avoid the requirement for separate metallic or other springs to be positioned between the latch 16 and the connector housing 34.

As shown most clearly in FIG. 4, the spring arms 122 extend in a generally linear but slightly curved orientation and away from the release button 66. The spring arms 122 each include a first end 124 connected to the release button 66 adjacent to the proximal face 42 of the connector housing 34. Therefore, the spring arms 122 project downwardly and distally to form a generally V-shaped cross section of the latch 16 at the spring arms 122. The free second ends 126 of the spring arms 122 are forced into engagement with at least one of the abutment surfaces 116 defined by the standoffs 108 within the interior cavity 106 and pad surfaces 128 defined across a bottom of the interior cavity 106 such as by the interior of the finger groove 72. When the latch 16 is fully inserted into the female connector component 14 as shown in the position of FIGS. 4 and 5, the spring arms 122 are typically at least partially deflected from an original position by either the abutment surfaces 116 and/or the pad surfaces 128. Accordingly, the spring arms 122 are constantly applying a force to push the release button 66 upwardly to the latched position, which is what is shown in these FIGS. 4 and 5.

Turning with reference now to FIG. 5, the latch plate 120 of the latch 16 is shown in cross section as it extends through the axial gap and along the latch track 112 in the latched position. The latch plate 120 includes a generally rectangular shaped plate defined by opposing side beams 130 extending from the release button 66 down to a curved occluding portion 132 extending across the bottom of the latch plate 120 adjacent to the opening 38 in the female distal end 36 and configured to be substantially aligned with the contour of the rounded bottom surface 68 in the latched position as shown in FIG. 5. The opposing side beams 130 include radially outwardly facing edges 134 including opposing projections 136 configured to snap into engagement with the detents 114 on the latch track 112. The abutment of these opposing projections 136 with the detents 114 prevents the latch 16 from being forced upwardly beyond the latched position shown in these figures. Moreover, the latch plate 120 is guided to move upwardly and downwardly transverse to the axial direction by the latch track 112.

The opposing side beams 130 and curved occluding portion 132 define an elongate latch opening 138 axially through the rectangular shaped plate and located below the release button 66. This elongate latch opening 138 is large enough to receive the male distal end 24 of the male connector component 12 in both the latched and unlatched positions described in further detail below. The curved occluding portion 132 includes a tapered lead-in surface 140 facing towards the opening 38 in the female distal end 36 and located in the latching position across at least a portion of the receptacle 40, as most clearly shown in FIG. 5. This tapered lead-in surface 140 assists the male connector component 12 in automatically forcing the curved occluding portion 132 out of the way during insertion of the male distal end 24 into the receptacle 40, also described in further detail below.

With the unitary or integrally formed latch 16 of this invention, the assembly of the female connector component 14 is a simple one-step process. After the latch 16 has been molded or manufactured so as to include the release button 66, the latch plate 120, and the spring arms 122 as a single piece of material and after the connector housing 34 is formed with the second fluid conduit 30, the latch 16 is pushed downwardly through the top side 62 of the connector housing 34 so that the opposing side beams 130 of the latch plate 120 engages with the latch track 112. The latch track 112 formed by the standoffs 108 will deform slightly outwardly to enable passage of the thickest portion of the latch plate 120 at the opposing projections 136. Once the opposing projections 136 snap into engagement with the detents 114 in the latch track 112, the spring arms 122 will be slightly deflected and will therefore bias the latch 16 to remain in this latched position. With this single assembly step, the female connector component 14 is ready for use with the male connector component 12 to form the fluid conduit connector 10.

In addition to reducing the complexity and time needed to assemble the female connector component 14, the integrally formed spring arms 122 on the latch also provide additional benefits. To this end, the integral connection of the spring arms 122 to the release button 66 minimizes or eliminates any connector failures caused by misalignments and movements of spring elements relative to the latch 16. Moreover, the provision of two redundant spring arms 122 on either side of the release button 66 ensures that even if one of the spring arms 122 were to break or lose resiliency, the other spring arm 122 would still bias the latch 16 into the latched position shown in FIGS. 4 and 5. Such redundancy would increase complexity and cost in conventional connector assemblies with separated parts, but not in the present invention because the integral formation of the latch 16 keeps the assembly a one-step process.

Figure 6:
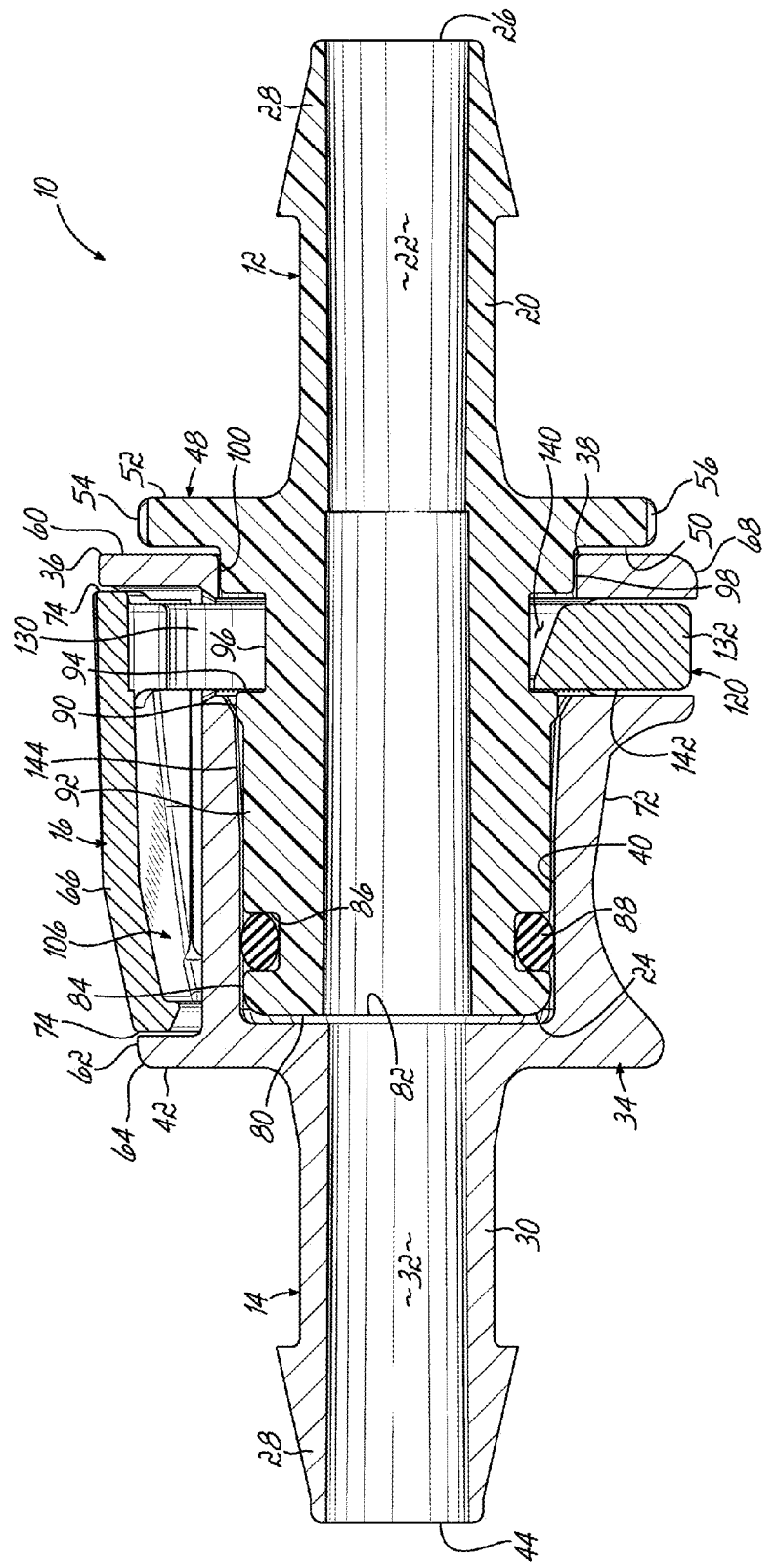
FIG. 6 is a cross-sectional side view of the fluid conduit connector of FIG. 1, showing internal features of the male and female connector components following insertion of the male connector component into a receptacle of the female connector component, including a latch in a latched position.
Figure 7A:
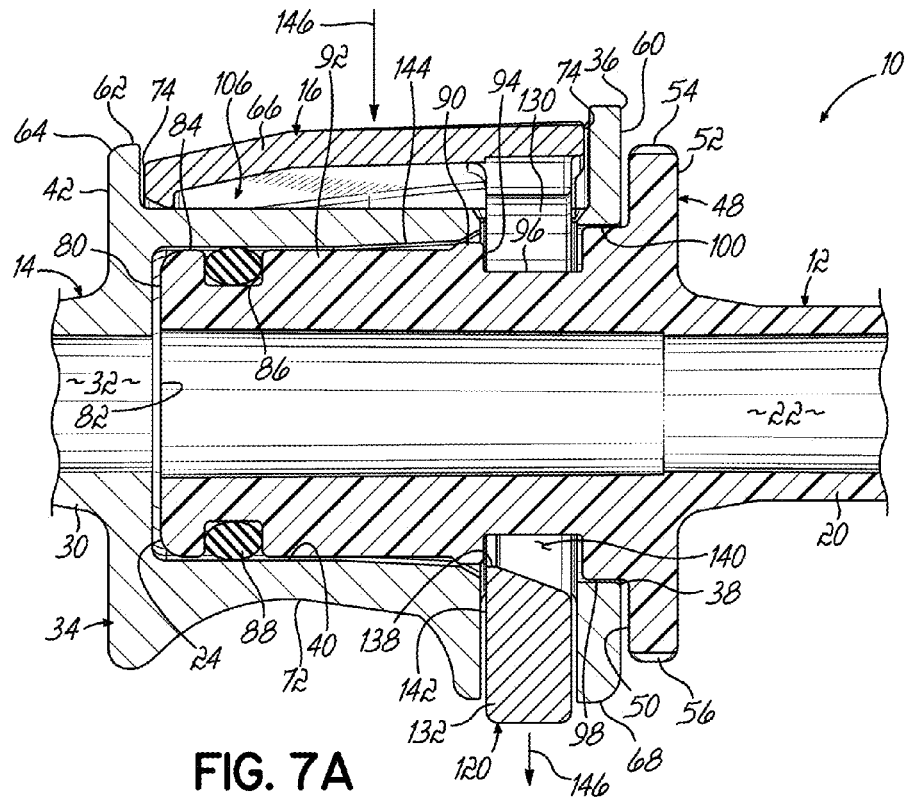
FIG. 7A is a cross-sectional side view of the fluid conduit connector of FIG. 6 following a depressing of the latch downwardly to an unlatched position.
Figure 7B:
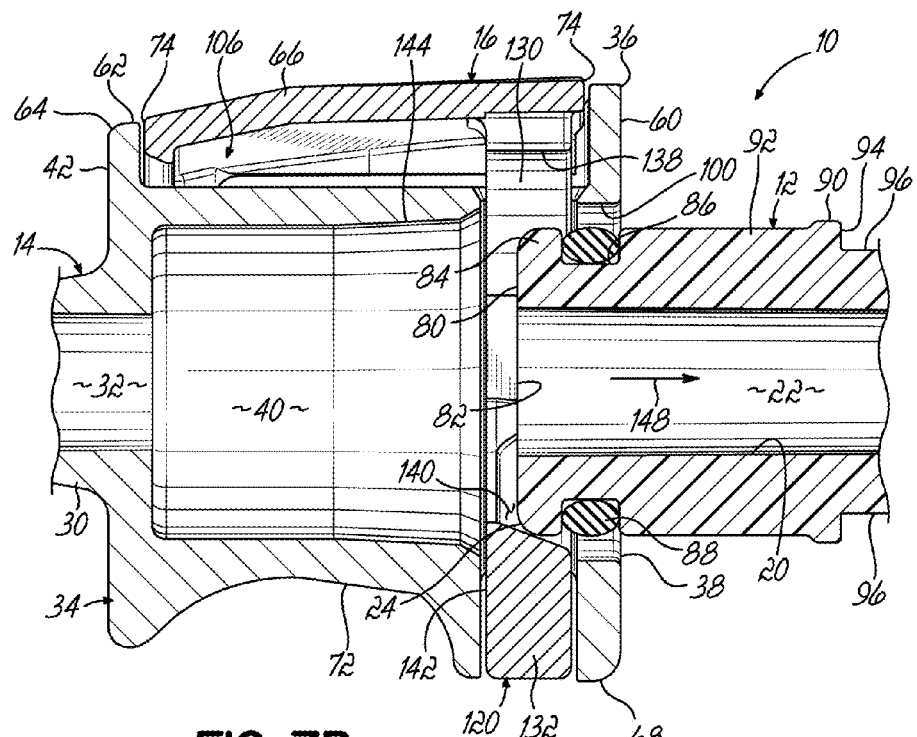
FIG. 7B is a cross-sectional side view of the fluid conduit connector of FIG. 7A during removal of the male connector component back out of the receptacle of the female connector component.

Further details of the fluid conduit connector 10 and the connecting and disconnecting operation enabled by the fluid conduit connector 10 are shown in FIGS. 6 through 7B. Beginning with FIG. 6, this cross-sectional view of the fluid conduit connector 10 shows the male and female connector components 12, 14 assembled into a sealed connection. To reach this position from an initial separated position shown in FIG. 2, the male distal end 24 is first inserted into and through the opening 38 at the female distal end 36. The male distal end 24 will then run into the tapered lead-in surface 140 of the curved occluding portion 132 of the latch plate 120, which extends across a portion of the receptacle 40 and thereby blocks the male distal end 24. However, the continued insertion of the male distal end 24 and the seal flange 84 towards the receptacle 40 will force the tapered lead-in surface 140 to ride downwardly in a transverse direction to the axial direction that the male connector component 12 is moving. This movement forces the latch 16 into the unlatched position, and the spring arms 122 are further deflected from the original position. Once the male distal end 24 has been inserted into the receptacle 40 to the extent where the latch plate 120 encounters the latch catch groove 96, the curved occluding portion 132 of the latch plate 120 will snap into engagement with the latch catch groove 96 since the male connector component 12 no longer blocks a return of the latch 16 to the latched position. Upon the return to the latched position, the latch 16 retains the male connector component 12 by being inserted into the latch catch groove 96 as shown in FIG. 6.

Although the curved occluding portion 132 of the latch plate 120 includes the tapered lead-in surface 140 facing distally towards the opening 38 in the female distal end 36, in order to enable automatic movement of the latch 16 out of the way during insertion of the male connector component 12 into the female connector component 14, the curved occluding portion 132 also includes a radial flat surface 142 dropping off at 90 degrees from the axial direction and facing proximally on the other side of the tapered lead-in surface 140. This radial flat surface 142 rigidly abuts the shoulder 94 of the latching flange 90 delimiting the latch catch groove 96 in order to prevent the latch 16 from unlatching just by pulling the male connector component 12 back away from the receptacle 40. This abutment of the radial flat surface 142 and the shoulder 94 is shown in FIG. 6. Consequently, the latch 16 must be intentionally actuated by depressing the release button 66 against the bias of spring arms 122 to move into the unlatched position in order to enable disconnection of the male connector component 12 from the female connector component 14.

Once the latch 16 has releasably engaged with the latch catch groove 96, the fluid conduit connector 10 is in a fully assembled state as shown in FIGS. 1 and 6. In this fully assembled state, the first and second elongate bores 22, 32 are located substantially adjacent to one another for fluid communication directly from the first fluid conduit 20 to the second fluid conduit 30 (or vice versa). A small gap may remain between the male distal end 24 and the receptacle 40, but the seal member 88 is sealingly engaged with the wall of the receptacle 40 in this fully assembled position to block any leakage or pressure loss from the first and second elongate bores 22, 32. Therefore, contamination to and from the flexible tubing portions is prevented, making the fluid conduit connector 10 suitable for use in hygienic applications such as in biopharmaceutical fluid management. Furthermore, in the fully assembled state, the adjacent or engaged relationship between the plurality of lugs 98 and the slightly conical annular periphery 100 as well as between the distal face 50 of the grip flange 48 and the female distal end 36 are shown in these views. These engagements assist with transfer of any side load or axial load applied to one or both of the male and female connector components 12, 14.

Because the seal member 88 tends to form a highly frictional resistance to movement against the receptacle 40, the receptacle 40 is also formed in this embodiment with an elongate tapered lead-in bore section 144 that reduces in size along a substantial portion of the receptacle 40 as shown in FIGS. 7A and 7B. Accordingly, the seal member 88 does not enter the high frictional engagement with the receptacle 40 until the male distal end 24 is nearly fully inserted into the receptacle 40. Therefore, the resistance to movement into and out of the fully assembled position is reduced in this fluid conduit connector 10 compared to conventional designs without the elongate tapered lead-in bore section 144.

When it is necessary to disconnect the male and female connector components 12, 14 from the fully assembled position shown in FIG. 6, a user grasps the female connector component 14 at the finger groove 72 and at the release button 66. The user then depresses the release button 66 downwardly into the interior cavity 106 of the connector housing 34 against the bias of the spring arms 122 such as indicated by arrow 146 in FIG. 7A. This downward movement transverse to the axial direction to an unlatched position causes the curved occluding portion 132 of the latch plate 120 to be moved out of engagement with the latch catch groove 96 in the male connector component 12. After reaching this unlatched position, the user grasps the male connector component 12 such as at the grip flange 48 and pulls the male distal end 24 away from the receptacle 40 as indicated by arrow 148 in FIG. 7B. Once the male distal end 24 is completely removed from the receptacle 40, the male connector component 12 no longer pushes the latch 16 into the unlatched position and the latch 16 returns as a result of bias of the spring arms 122 back to the latched position as shown in FIG. 7B. The male and female connector components 12, 14 are then ready for re-connection simply by reversing the steps described above to move from the position shown in FIG. 7B to the position shown in FIG. 6 again.

As discussed in detail above, the first embodiment of the fluid conduit connector 10 provides several advantageous benefits in this field of connector assemblies. First, the integral formation of multiple spring arms 122 on the latch 16 provides both redundancy to protect against connector failure and a significantly simplified manufacturing and snap-in assembly process for the latch 16 and the connector housing 34. In addition, the latch 16 continues to automatically move out of the blocking or latched position when the male connector component 12 is inserted into the receptacle 40, thereby not requiring additional steps to connect the two connector components 12, 14. Each of the male and female connector components 12, 14 provides structures that make it easy to manually grasp and manipulate or move items such as the release button 66 on the latch 16. Moreover, the contoured outer surface presented by the connector housing 34 and button shroud 64 avoids exposing any sharp corners or edges 74 or pinch points that could catch on clothing or other equipment. The receptacle 40 also reduces frictional resistance to intended movements along the axial direction as a result of the tapered lead-in bore section 144. Consequently, the fluid conduit connector 10 of this embodiment provides numerous improvements to the connector assembly field.

With reference to FIGS. 8 through 13, an alternative embodiment of the female connector component 160 used with the fluid conduit connector 10 is shown in detail. This alternative female connector component 160 includes a lock mechanism 162 that interacts with the latch 16 and with the connector housing 34 to provide additional security against unintentional disconnection of the male and female connector components 12, 160. The vast majority of features and elements described in connection with the latch 16 and the female connector component 14 in the embodiment of FIGS. 1 through 7B are also present and operate in the same manner in this embodiment. Where those features are unchanged, the same reference numbers have been applied in the drawing figures without additional explanation in the description below. Modified elements have been provided with new reference numbers where appropriate, but it will be understood that more or fewer components may be modified to accommodate the addition of the lock mechanism 162 without departing from the scope of the present invention.

Figure 8:
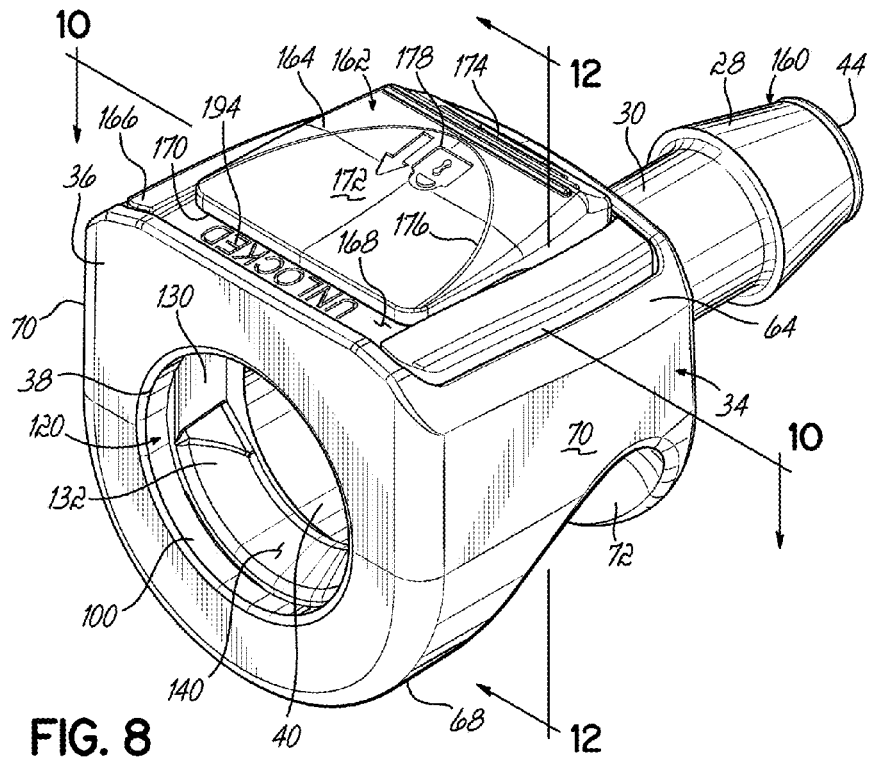
FIG. 8 is a perspective view of a female connector component according to a second embodiment of the present invention, the female connector component including a latch and a lock mechanism shown in an unlocked position.
Figure 9:
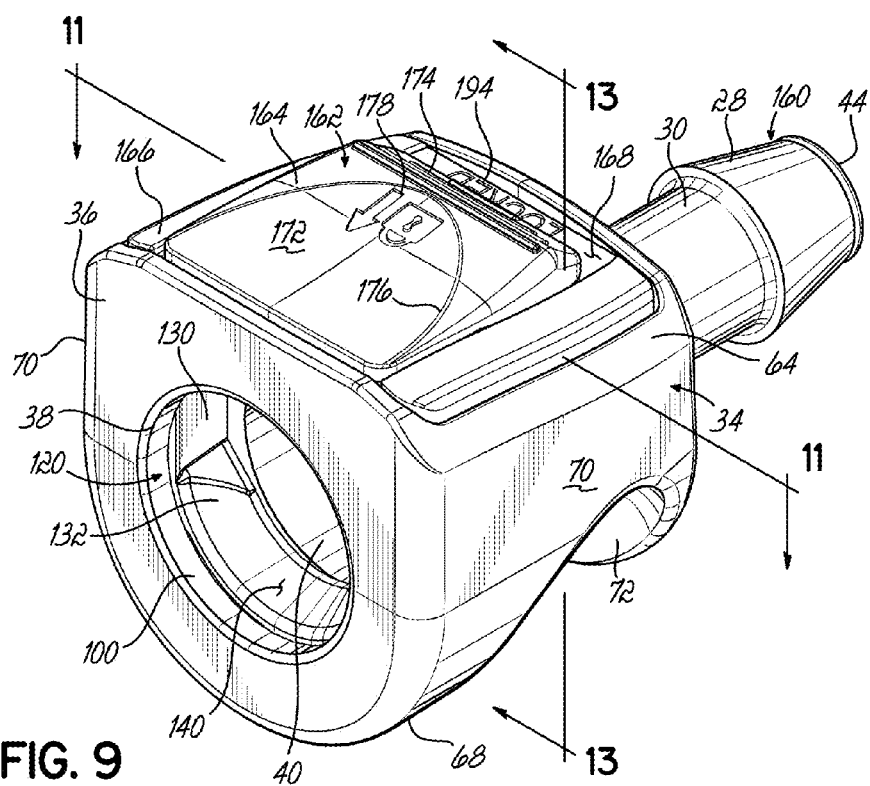
FIG. 9 is a perspective view of the female connector component of FIG. 8 with the lock mechanism moved to a locked position.

As shown in FIGS. 8 and 9, this embodiment of the female connector component 160 includes the lock mechanism 162, which is defined by a lock slider 164 operatively engaged with a modified version of the release button 166 on the latch 16. The modified release button 166 includes some new aperture features described further below for interaction with the lock slider 164, but otherwise is only modified by removing some thickness to make space for the lock slider 164 to be installed on top of the release button 166. Consequently, the remainder of the latch 16, including the latch plate 120 and the spring arms 122, operate the same in this embodiment (e.g., automatic movement from latched position to unlatched position when inserting the male connector component 12, and manual depressing of the release button 166 against the spring bias to move back to the unlatched position) as in the previously described embodiment. Accordingly, the locking version of the female connector component 160 still provides all of the same advantages described above in connection with the first embodiment.

The lock slider 164 is shown in further detail in FIGS. 10 through 13. To this end, the lock slider 164 is a substantially planar member configured to slide along a generally planar top surface 168 of the release button 166 between a proximal unlocked position and a distal locked position. It will be appreciated that the unlocked and locked positions may be reversed by arranging some internal components differently in other embodiments. The lock slider 164 includes a substantially planar lower surface 170, which is positioned to slide along the top surface 168 of the release button 166, and a contoured upper surface 172 facing outwardly from the female connector component 160. The contoured upper surface 172 may include a grip ridge 174 configured to be pressed by the user when the lock slider 164 is moved between locked and unlocked positions and also include a finger depression 176 provided for additional grip. The contoured upper surface 172 may also include a first visual indicia 178 configured to identify which movement direction causes the lock slider 164 to be in the locked position. Therefore, a user can readily understand and be assisted in moving the lock slider 164 between positions as a result of the contoured upper surface 172 and the first visual indicia 178.

The lock mechanism 162 also includes a pair of lock lugs 180 extending downwardly from the lower surface 170 of the lock slider 164. The pair of lock lugs 180 is inserted through elongated lug apertures 182 provided through the release button 166 of the latch 16. In this regard, the lock lugs 180 extend into the interior cavity 106 formed in the connector housing 34. Each of the lock lugs 180 includes a retention detent 184 extending laterally outward from the lock lug 180 so as to snap into engagement under a corresponding elongate fin 186 projecting downwardly from the release button 166 adjacent to each of the lug apertures 182. As shown most clearly in FIGS. 12 and 13, the retention detent 184 slides along the fin 186 to prevent the lock lugs 180 and lock slider 164 from being unintentionally pulled off of the latch 16. In addition, the lock lugs 180 provide an easy method for assembling the lock mechanism 162 with the latch 16 in this embodiment, as all that needs to be done is inserting the lock lugs 180 through the lug apertures 182 and snapping the retention detents 184 into engagement with the fins 186. It will be understood that other retention structures known in the art may be used to hold the lock mechanism 162 to the latch 16 in other embodiments of the present invention.

The lock mechanism 162 further includes a spring pin 188 extending downwardly from the lock slider 164 so as to be inserted through a shaped aperture 190 (shaped as a figure-8 in the illustrated embodiment) provided through the release button 166 of the latch 16. The figure-8 shaped aperture 190 in the release button 166 is configured to deform so as to enable the spring pin 188 to move from a first portion of the figure-8 shaped aperture 190 when in the locked position to a second portion of the figure-8 shaped aperture 190 when in the unlocked position. In this regard, the user must apply sufficient force to slide the lock slider 164 between these positions, which requires the temporary deformation of the figure-8 shaped aperture 190 with the spring pin 188. It will be understood that the spring pin 188 may be formed so as to be the deforming member (such as by being split into two resilient portions movable relative to one another) during movement between the two portions of the shaped aperture 190. For example, the shaped aperture 190 may be reshaped to define a generally dog-bone (or barbell) shape with two larger ends joined by an elongated narrow corridor that forces deformation or contraction of the deformable spring pin 188 in order to move through the narrow corridor from one end position to another end position (e.g., the locked and unlocked positions). In any event, the engagement of the spring pin 188 with this shaped aperture 190 in the release button 166 prevents unintentional movements of the lock slider 164 between the locked and unlocked positions. It will be understood that a different structure may be provided on the lock slider 164 and the release button 166 to retain the lock slider 164 in the locked and unlocked positions in other embodiments consistent with the scope of the invention.

Figure 10:
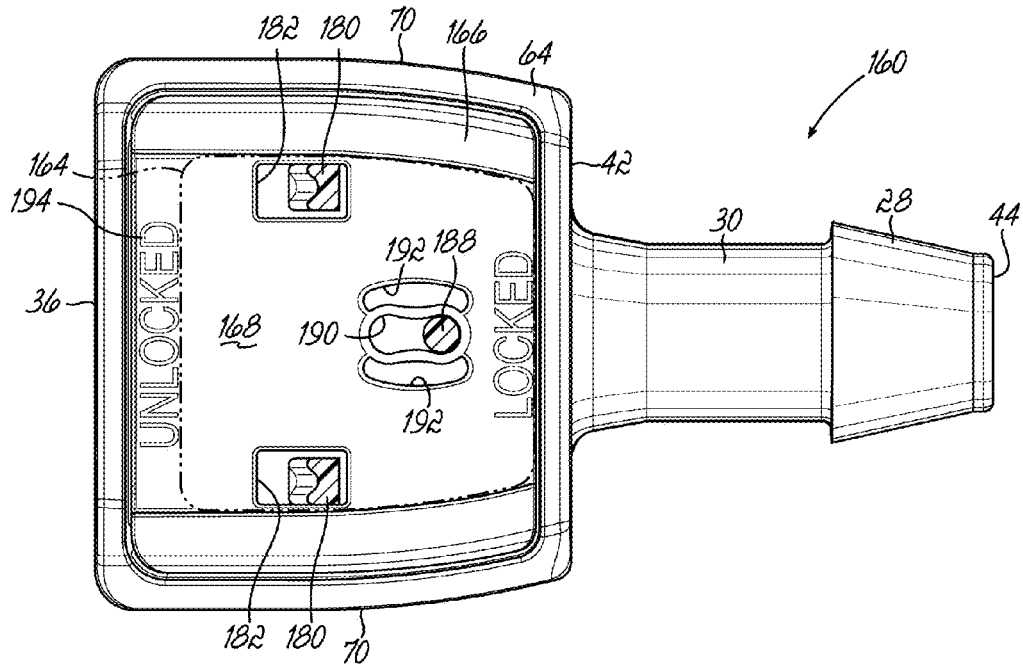
FIG. 10 is a cross-sectional top view of the female connector component of FIG. 8 along line 10-10 to show features of the lock mechanism interacting with features of the latch in the unlocked position.
Figure 11:
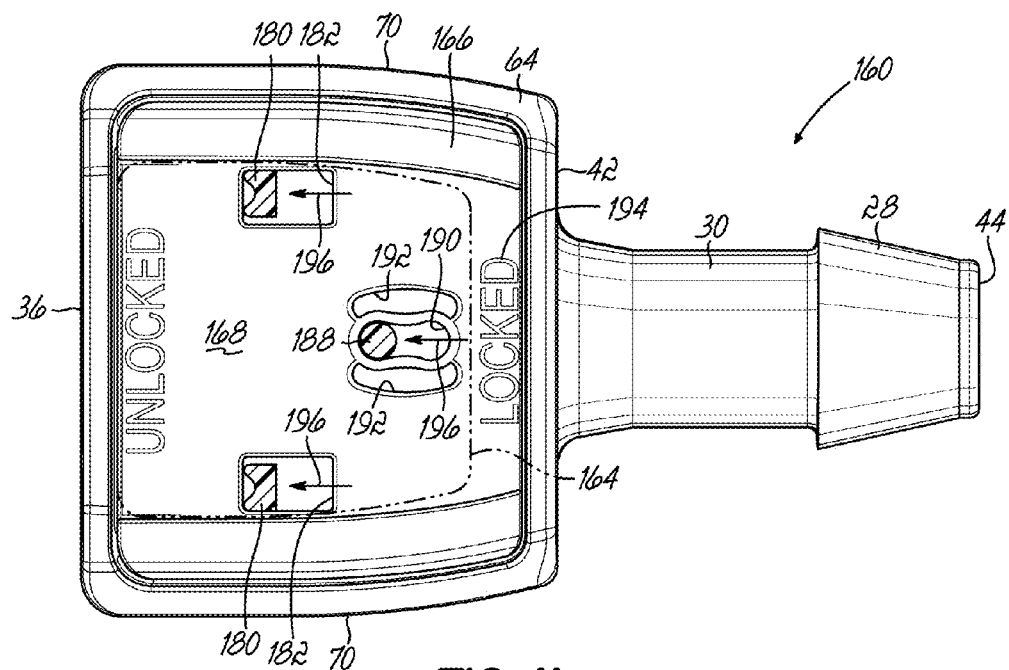
FIG. 11 is a cross-sectional top view of the female connector component of FIG. 9 along line 11-11 to show features of the lock mechanism interacting with features of the latch in the locked position.

As shown in FIGS. 10 and 11, the figure-8 shaped aperture 190 of this embodiment is surrounded by adjacent deformation apertures 192 extending through the release button 166. These deformation apertures 192 provide the space needed for the figure-8 shaped aperture 190 to deform outwardly when the spring pin 188 moves between the locked and unlocked positions. Also evident from FIGS. 10 and 11, the top surface 168 of the release button 166 includes second visual indicia 194 in the form of the words "LOCKED" and "UNLOCKED," which may be alternatively revealed or uncovered to show the current state of the lock mechanism 162. Accordingly, a user can quickly glance at the female connector component 160 and the top surface 168 to determine whether the lock mechanism 162 is in a locked state or not.

Figure 12:
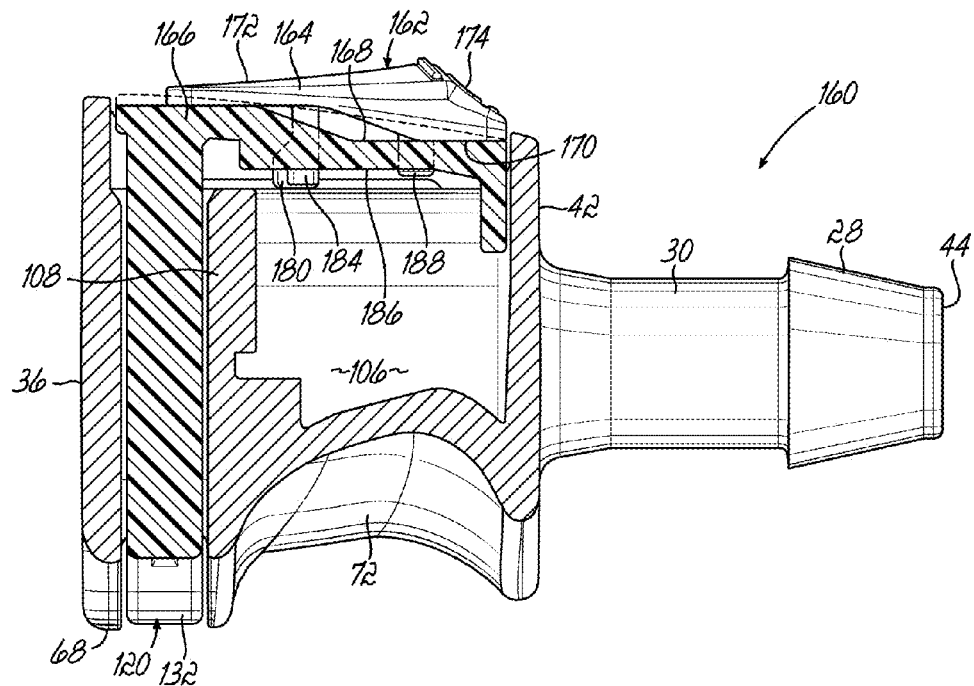
FIG. 12 is a cross-sectional side view of the female connector component of FIG. 8 along line 12-12 to show features of the lock mechanism interacting with features of a connector housing in the unlocked position.
Figure 13:
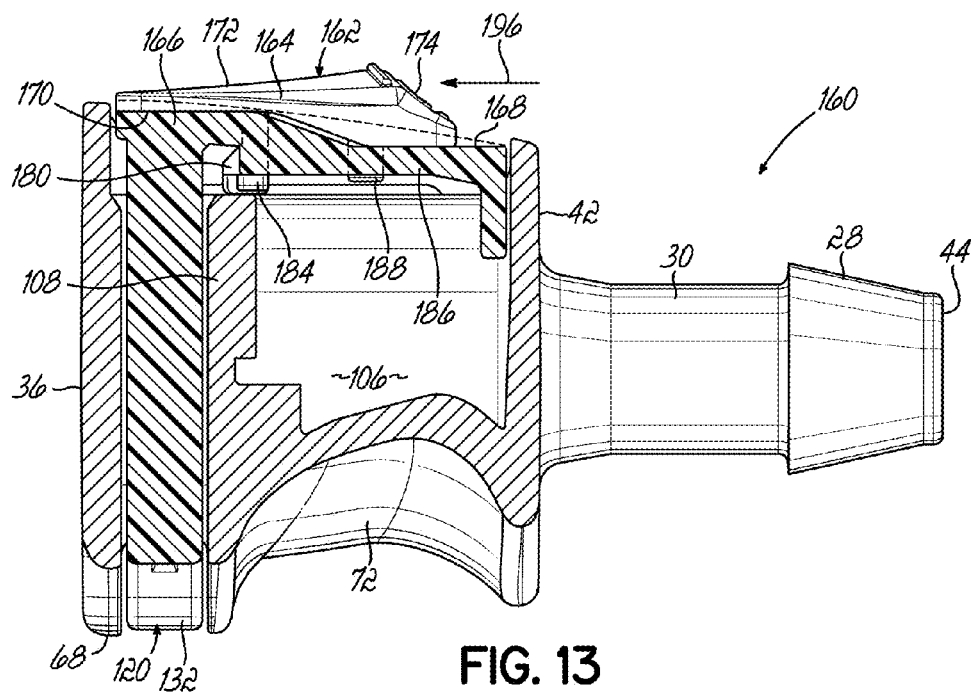
FIG. 13 is a cross-sectional side view of the female connector component of FIG. 9 along line 13-13 to show features of the lock mechanism interacting with features of a connector housing in the locked position.

The lock mechanism 162 is configured to interact with a standoff within the interior cavity 106 of the connector housing 34. To this end, the standoffs 108 described in connection with the previous embodiment may also be used to interact with the lock lugs 180 of this embodiment. If necessary, it will be understood that the standoffs 108 could be modified to extend to a position in which the lock lugs 180 can interact with the standoffs 108. As shown most particularly in the cross-sectional views of FIGS. 12 and 13, the lock lugs 180 move from a location over an empty portion of the interior cavity 106 in the unlocked position to another location over the standoffs 108 in the locked position (this movement shown by arrow 196 in FIGS. 11 and 13). In the locked position, downward movement of the lock lugs 180 (and therefore also downward movement of the release button 166) is prevented by the abutment of the lock lugs 180 and the standoffs 108 located underneath the lock lugs 180. In this position, the latch 16 cannot be automatically or manually moved from the latched position to the unlatched position. When the lock lugs 180 are positioned over the empty portion of the interior cavity 106 as shown in FIG. 12, there is no structure blocking downward movement of the lock lugs 180 and the release button 166. Therefore, the release button 166 and the latch 16 may be actuated normally between the latched and unlatched positions when the lock mechanism 162 is in the unlocked position.

The addition of the lock mechanism 162 to the female connector component 160 of this embodiment allows for a positive securing of the latch 16 in the latched position, which may be desirable in high load or high pressure fluid applications, among others. In addition, the lock mechanism 162 is also formed as a unitary piece including the lock slider 164, the lock lugs 180, and the spring pin 188 for one-step snap-on assembly to the release button 166 of the latch 16. Consequently, the female connector component 160 is assembled in two easy steps, specifically, snapping the lock mechanism 162 on the latch 16 and snapping the latch 16 into the connector housing 34 (these snap connections may be performed in any order). The lock mechanism 162 is configured for quick and easy actuation between the locked and unlocked positions, which provides additional benefits and protection in addition to those described above for the first embodiment. In sum, the fluid conduit connector 10 of all described embodiments enables reliable secured connection of fluid conduits with a simple to manufacture and use assembly.

While the present invention has been illustrated by a description of various preferred embodiments and while these embodiments have been described in some detail, it is not the intention of the Applicant to restrict or in any way limit the scope of the appended claims to such detail. Additional advantages and modifications will readily appear to those skilled in the art. The various features of the invention may be used alone or in any combination depending on the needs and preferences of the user. This has been a description of the present invention, along with the preferred methods of practicing the present invention as currently known. However, the invention itself should only be defined by the appended claims.

What is claimed is:

1. A female connector component configured to be coupled to a male connector component comprising a first fluid conduit and a latch catch groove, the female connector component comprising:
   a connector housing defining a proximal end, a female distal end and a receptacle extending proximally from an opening in said female distal end;
   a second fluid conduit defined by a second elongate bore extending from said receptacle;
   a latch operatively engaged with said connector housing for releasably retaining the male connector component, said latch including:
      a release button positioned along a side of said connector housing,
      a latch plate extending from said release button at least partially across said receptacle and configured to latch into engagement with the male connector component, and
      at least one spring arm integrally formed as a unitary piece with said release button and extending into said connector housing, said at least one spring arm engaging said connector housing to bias said latch towards a latched position in which said latch plate engages the latch catch groove to prevent removal of the male connector component from said receptacle, said release button configured to be depressed into said connector housing to move said latch against the bias and towards an unlatched position in which said latch plate disengages from the latch catch groove; and
   a lock mechanism comprising a lock slider operatively engaged with said latch, said lock slider being slidable distally and proximally along the side of said connector housing between a locked position, in which movement of said latch towards the unlatched position is prevented, and an unlocked position where operation of said latch is unaffected.

2. The female connector component of claim 1, wherein said lock mechanism further includes at least one lock lug extending downwardly from said lock slider and through lug apertures in said release button, and wherein said female connector component further comprises:
   a standoff projecting inwardly from said connector housing and outwardly from said receptacle to be located underneath said at least one lock lug when said lock slider is moved to the locked position, thereby preventing further downward movement of said lock slider and said latch away from the latched position.

3. The female connector component of claim 2, wherein said latch includes at least one fin projecting downwardly from said release button adjacent to said at least one lock lug, and wherein said at least one lock lug includes a retention detent configured to snap into engagement with said at least one fin to maintain said lock mechanism in position on said latch.

4. The female connector component of claim 1, wherein said latch further includes a shaped aperture and said lock mechanism further includes a spring pin extending downwardly from said lock slider into engagement within said shaped aperture, the engagement of said spring pin and said shaped aperture preventing unintentional movements of said lock slider between the locked and unlocked positions.

5. The female connector component of claim 1, wherein said release button of said latch further includes visual indicia revealed by movement of said lock slider to indicate whether said lock mechanism is in the locked or unlocked position.

6. The female connector component of claim 1, wherein the release button is positioned along a top side of said connector housing.

7. The female connector component of claim 1, wherein the lock slider comprises visual indicia identifying the direction of movement to the locked position.

8. A quick connect fluid conduit connector, comprising:
   a male connector component including a male distal end configured to receive a seal member, a first fluid conduit defined by a first elongate bore extending from said male distal end, and a latch catch groove adjacent to a radially projecting latching flange located proximally from said male distal end; and
   the female connector component of claim 1.

9. The quick connect fluid conduit connector of claim 8, wherein said latch includes multiple spring arms integrally formed as a unitary piece with said release button for redundantly biasing said latch towards the latched position.

10. The quick connect fluid conduit connector of claim 8, wherein said receptacle further includes a tapered lead-in bore section extending proximally from said latch plate of said latch, said tapered lead-in bore section configured to reduce frictional engagement between said receptacle and said seal member on said male connector component during insertion or removal of said male distal end relative to said receptacle.

11. The quick connect fluid conduit connector of claim 8, wherein said opening in said female distal end is bounded by a generally annular periphery, and wherein said male connector component further includes a plurality of lugs located proximal to said latch catch groove that are configured to engage said generally annular periphery of said opening after insertion of said male connector component into said receptacle and configured to at least partially transfer radial or side loads between said male connector component and said female connector component.

12. The quick connect fluid conduit connector of claim 11, wherein said latch catch groove is delimited on one side by said radially projecting latching flange and delimited on another side by said plurality of lugs.

13. The quick connect fluid conduit connector of claim 11, wherein said male connector component further includes a radially extending grip flange located adjacent to said plurality of lugs, and wherein said grip flange is positioned to abut said female distal end after insertion of said male connector component into said receptacle to at least partially transfer axial loads between said male connector component and said female connector component.

14. The quick connect fluid conduit connector of claim 8, wherein said latch plate includes an occluding portion extending into said receptacle in the latched position of said latch to thereby engage said latch catch groove on said male connector component, and said occluding portion includes a tapered lead-in surface facing towards said opening in said female distal end such that insertion of said male distal end into said receptacle automatically forces said occluding portion downward to move said latch into the unlatched position during the insertion.

15. The quick connect fluid conduit connector of claim 8, wherein said connector housing further includes a contoured button shroud defining said side of said connector housing and surrounding sharp edges of said release button.

16. The quick connect fluid conduit connector of claim 8, wherein said connector housing further includes a bottom surface facing in an opposite direction from said side including the release button, said bottom surface defining a finger groove projecting inwardly towards said side to provide a grip location opposite said release button.

17. The quick connect fluid conduit connector of claim 16, wherein said finger groove and said release button each extend in an axial direction along a majority of said connector housing between said female distal end and said second fluid conduit.

18. The quick connect fluid conduit connector of claim 8, wherein said lock mechanism further includes at least one lock lug extending downwardly from said lock slider and through lug apertures in said release button, and wherein said female connector component further comprises:
  a standoff projecting inwardly from said connector housing and outwardly from said receptacle to be located underneath said at least one lock lug when said lock slider is moved to the locked position, thereby preventing further downward movement of said lock slider and said latch away from the latched position.

19. The quick connect fluid conduit connector of claim 18, wherein said latch includes at least one fin projecting downwardly from said release button adjacent to said at least one lock lug, and wherein said at least one lock lug includes a retention detent configured to snap into engagement with said at least one fin to maintain said lock mechanism in position on said latch.

20. The quick connect fluid conduit connector of claim 8, wherein said latch further includes a shaped aperture and said lock mechanism further includes a spring pin extending downwardly from said lock slider into engagement within said shaped aperture, the engagement of said spring pin and said shaped aperture preventing unintentional movements of said lock slider between the locked and unlocked positions.

21. The quick connect fluid conduit connector of claim 8, wherein said release button of said latch further includes visual indicia revealed by movement of said lock slider to indicate whether said lock mechanism is in the locked or unlocked position.

22. The quick connect fluid conduit connector of claim 8, wherein each of said male connector component, said female connector component, and said latch is integrally molded from polypropylene material.

23. A female connector component configured to be coupled to a male connector component comprising a first fluid conduit and a latch catch groove, the female connector component comprising:
  a connector housing defining a female distal end and a receptacle extending proximally from an opening in said female distal end;
  a second fluid conduit defined by a second elongate bore extending from said receptacle;
  a standoff projecting inwardly from said connector housing and outwardly from said receptacle;
  a latch operatively engaged with said connector housing for releasably retaining the male connector component, said latch including:
    a release button positioned along a side of said connector housing,
    a latch plate extending from said release button at least partially across said receptacle and configured to latch into engagement with the male connector component, and
    at least one spring arm integrally formed as a unitary piece with said release button and extending into said connector housing, said at least one spring arm engaging said connector housing to bias said latch towards a latched position in which said latch plate engages the latch catch groove to prevent removal of the male connector component from said receptacle, said release button configured to be depressed into said connector housing to move said latch against the bias and towards an unlatched position in which said latch plate disengages from the latch catch groove; and
  a lock mechanism comprising:
    a lock slider operatively engaged with said latch, said lock slider being movable between a locked position, in which movement of said latch towards the unlatched position is prevented, and an unlocked position where operation of said latch is unaffected; and
    at least one lock lug extending downwardly from said lock slider and through lug apertures in said release button,
  wherein the standoff is located underneath said at least one lock lug when said lock slider is moved to the locked position, thereby preventing further downward movement of said lock slider and said latch away from the latched position.

24. A female connector component configured to be coupled to a male connector component comprising a first fluid conduit and a latch catch groove, the female connector component comprising:
- a connector housing defining a female distal end and a receptacle extending proximally from an opening in said female distal end;
- a second fluid conduit defined by a second elongate bore extending from said receptacle;
- a latch operatively engaged with said connector housing for releasably retaining the male connector component, said latch including:
  - a release button positioned along a side of said connector housing,
  - a latch plate extending from said release button at least partially across said receptacle and configured to latch into engagement with the male connector component,
  - at least one spring arm integrally formed as a unitary piece with said release button and extending into said connector housing, said at least one spring arm engaging said connector housing to bias said latch towards a latched position in which said latch plate engages the latch catch groove to prevent removal of the male connector component from said receptacle, said release button configured to be depressed into said connector housing to move said latch against the bias and towards an unlatched position in which said latch plate disengages from the latch catch groove, and
  - a shaped aperture; and
- a lock mechanism comprising:
  - a lock slider operatively engaged with said latch, said lock slider being movable between a locked position, in which movement of said latch towards the unlatched position is prevented, and an unlocked position where operation of said latch is unaffected; and
  - a spring pin extending downwardly from said lock slider into engagement within said shaped aperture, the engagement of said spring pin and said shaped aperture preventing unintentional movements of said lock slider between the locked and unlocked positions.

* * * * *